United States Patent
Thiel et al.

(10) Patent No.: US 10,975,024 B2
(45) Date of Patent: Apr. 13, 2021

(54) CRYSTAL COMPOSITION (CC) COMPRISING 4,4#-DICHLORODIPHENYLSULFOXIDE CRYSTALS (C)

(71) Applicant: BASF SE, Ludwigshafen am Rhein (DE)

(72) Inventors: Indre Thiel, Ludwigshafen (DE); Christian Schuetz, Ludwigshafen (DE); Stefan Blei, Ludwigshafen (DE); Jun Gao, Ludwigshafen (DE); Lukas Metzger, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/784,287

(22) Filed: Feb. 7, 2020

(65) Prior Publication Data

US 2020/0255374 A1    Aug. 13, 2020

Related U.S. Application Data

(60) Provisional application No. 62/802,983, filed on Feb. 8, 2019.

(30) Foreign Application Priority Data

Feb. 8, 2019   (EP) .................................... 19156145

(51) Int. Cl.
    *C07C 317/14*   (2006.01)
(52) U.S. Cl.
    CPC ........ *C07C 317/14* (2013.01); *C07C 2601/16* (2017.05)

(58) Field of Classification Search
    CPC .................................................. C07C 317/14
    See application file for complete search history.

(56) References Cited

U.S. PATENT DOCUMENTS

| | | | |
|---|---|---|---|
| 2,618,582 A | | 11/1952 | Buckmann |
| 6,197,924 B1 * | | 3/2001 | Takekoshi .............. C08G 65/46 528/497 |
| 2015/0111794 A1 * | | 4/2015 | Zia ....................... C10M 147/00 508/106 |

FOREIGN PATENT DOCUMENTS

| | | |
|---|---|---|
| RU | 2 159 764 C1 | 11/2000 |
| WO | WO 2019/034468 | 2/2019 |
| WO | WO 2019/034469 | 2/2019 |
| WO | WO 2019/034470 | 2/2019 |
| WO | WO 2019/034473 | 2/2019 |
| WO | WO 2020/007634 | 1/2020 |
| WO | WO 2020/043517 | 3/2020 |

OTHER PUBLICATIONS

Weber et al. Crystallization in Polyamide 6/Polysulfone Blends: Effect of Polysulfone Particle Size. Macromolecules, vol. 31, 4963-4969. (Year: 1998).*

* cited by examiner

*Primary Examiner* — Sikarl A Witherspoon
(74) *Attorney, Agent, or Firm* — Oblon, McClelland, Maier & Neustadt, L.L.P.

(57) ABSTRACT

The invention relates to a crystal (C) consisting of at least 95% by weight of 4,4'-dichlorodiphenylsulfoxide, 0 to 2% by weight of impurities and 0 to 3% by weight of an organic solvent (os). Moreover, the present invention relates to a crystal composition (CC) comprising crystals (C) and a process for the production of the crystal composition (CC) and the crystal (C).

16 Claims, 10 Drawing Sheets

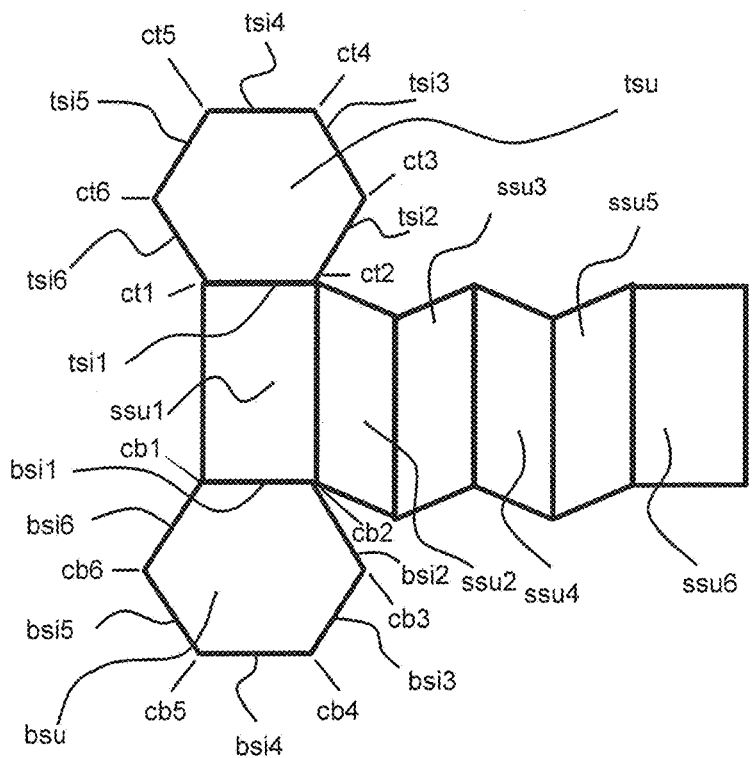
Fig. 1A
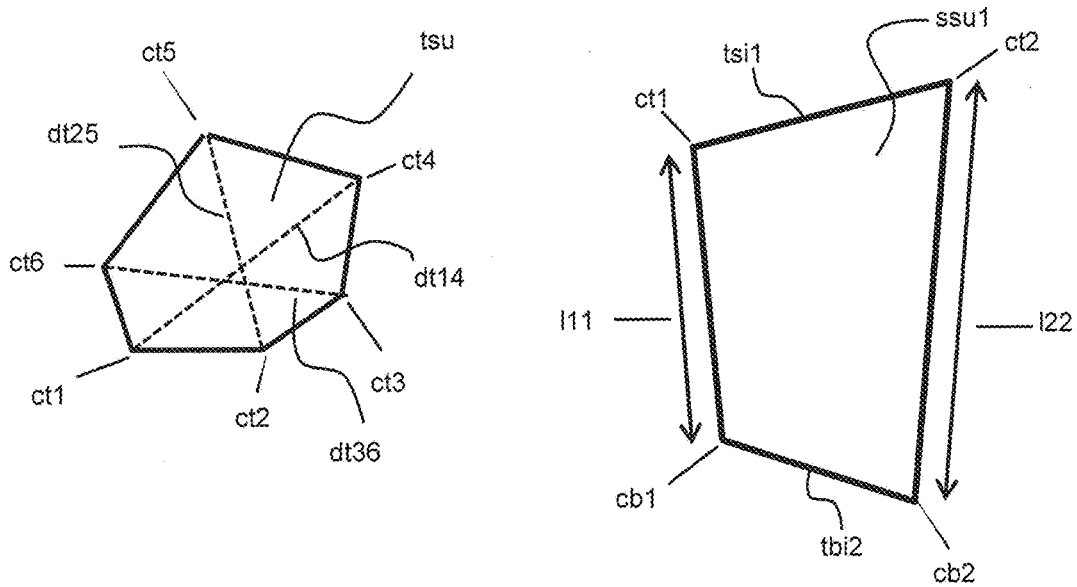
Fig. 1B
Fig. 1C

CRYSTAL COMPOSITION (CC) COMPRISING 4,4#-DICHLORODIPHENYLSULFOXIDE CRYSTALS (C)

The invention relates to a crystal (C) consisting of at least 95% by weight of 4,4'-dichlorodiphenylsulfoxide, 0 to 2% by weight of impurities and 0 to 3% by weight of an organic solvent (os). Moreover, the present invention relates to a crystal composition (CC) comprising crystals (C) and a process for the production of the crystal composition (CC) and the crystal (C).

4,4'-dichlorodiphenylsulfoxide is also called 1-chloro-4-(4-chlorophenyl)sulfinyl benzene or bis(4-chlorophenyl) sulfoxide. 4,4'-dichlorodiphenylsulfoxide is a white to pale yellow solid and has a molecular weight of 271.16 g/mol, a chemical formula $C_{12}$—$H_8$—$Cl_2$—OS and the CAS-registry-number of 4,4'-dichlorodiphenylsulfoxide is 3085-42-5, the chemical structure is as follows

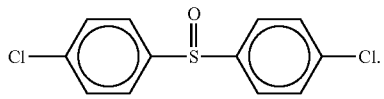

4,4'-dichlorodiphenylsulfoxide is commercially available, for example from abcr GmbH Switzerland, Alfa Aesar or TCI America.

For the production of 4,4'-dichlorodiphenylsulfoxide several processes are known. One common process is a Friedel-Crafts-Reaction with thionyl chloride and chlorobenzene as starting materials in the presence of a catalyst, for example aluminum(III)chloride or iron(III)chloride. Sun, X. et al, "*Iron(III) chloride (FeCl₃)-catalyzed electrophilic aromatic substitution of chlorobenzene with thionyl chloride (SOCl₂) and the accompanying auto-redox in sulfur to give diaryl sulfides (Ar₂S): Comparison to catalysis by aluminum chloride (AlCl₃)*", phosphorus, sulfur, and silicon, 2017, Vol. 192, No. 3, pages 376 to 380, and Sun, X. et al, "*Investigations on the Lewis-acids-catalysed electrophilic aromatic substitution reactions of thionyl chloride and selenyl chloride, the substituent effects, and the reaction mechanisms*", Journal of Chemical Research 2013, pages 736 to 744, discloses general processes for the production of 4,4'-dichlorodiphenylsulfoxide. In these documents the reaction mixture containing 4,4'-dichlordiphenylsulfoxide is poured into ice water. Subsequently diethylether is added and all the contents are added to a separation funnel and the organic product is extracted with diethylether. Then all the ether solutions are combined dried with sodium sulfate and filtered. Hereinafter the diethylether is removed to obtain 4,4'-dichlorodiphenylsulfoxide.

U.S. Pat. No. 2,618,582 discloses a process for the preparation of diaryldisulfoxides. In example II of U.S. Pat. No. 2,618,582, the preparation of di-p-(chlorophenyl)disulfoxide is disclosed, which is also named 4,4'-dichlorodiphenyldisulfoxide. This compound has a melting point of 136° C. and the following chemical structure:

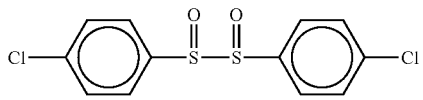

RU 2159764 C1 discloses a process for the preparation of 4,4'-dichlorodiphenylsulfoxide. The product is recrystallized from chloroform. RU 2158257 C1 also discloses a process for the preparation of 4,4'-dichlorodiphenylsulfoxide, wherein the product is recrystallized from ethyl acetate.

Commercially available 4,4'-dichlorodiphenylsulfoxide is provided in particulate powder form. In the processes described in the above mentioned documents 4,4'-dichlorodiphenylsulfoxide is also obtained in particulate powder form.

The powdery particulate 4,4'-dichlorodiphenylsulfoxides commercially available, and the powdery particulate 4,4'-dichlorodiphenylsulfoxides obtained in the processes described in the above mentioned documents, however, for some applications show insufficient flowability. Moreover, in some cases the content of by-product contained in the 4,4'-dichlorodiphenylsulfoxides or the APHA-color number is too high.

Therefore, the object underlying the present invention is to provide 4,4'-dichlorodiphenylsulfoxide in particulate form, which does not have the above-mentioned disadvantages of the prior art or has them only in a significantly reduced extent.

This object was solved by a crystal composition (CC) comprising crystals (C), wherein the crystals (C) consist of
 (a) at least 95% by weight of 4,4'-dichlorodiphenylsulfoxide,
 (b) 0 to 2% by weight of impurities and
 (c) 0 to 3% by weight of an organic solvent (os),
based on the total weight of the crystals (C) contained in the crystal composition (CC), wherein the crystal composition (CC) has
 a $d10_{,3}$-value in the range of 100 to 400 μm,
 a $d50_{,3}$-value in the range of 300 to 800 μm and
 a $d90_{,3}$-value in the range of 700 to 1500 μm,
wherein the $d10_{,3}$-value is lower than the $d50_{,3}$-value and the $d50_{,3}$-value is lower than the $d90_{,3}$-value.

It had been found that, surprisingly, the crystal composition (CC) shows a better flowability compared to the particulate 4,4'-dichlorodiphenylsulfoxides described in the state of the art. Moreover, it has been found that the crystals (C) comprised in the crystal composition have a low content of by-product, a low content of residual solvent as well as a low APHA-color number.

Crystal Composition (CC)

The crystal composition (CC) comprises crystals (C). In a preferred embodiment the crystal composition (CC) comprises at least 95% by weight of the crystals (C), more preferred the crystal composition (CC) comprises at least 98% by weight of crystals (C) even more preferred the crystal composition (CC) comprises at least 99% by weight of the crystals (C) and particularly preferred the crystal composition (CC) comprises at least 99.5% by weight of crystals (C) in each case based on the total weight of the crystal composition (CC). In an even more preferred embodiment the crystal composition (CC) consists of the crystals (C).

Therefore, another object of the present invention is a crystal composition (CC), wherein the crystal composition (CC) comprises at least 95% by weight of crystals (C), based on the total weight of the crystal composition (CC).

The crystal composition (CC) of the invention generally has:
 a $d10_{,3}$-value in the range of 100 to 400 μm,
 a $d50_{,3}$-value in the range of 300 to 800 μm and
 a $d90_{,3}$-value in the range of 700 to 1500 μm.

Preferably, the crystal composition (CC) of the invention has:
a $d10_{,3}$-value in the range of 200 to 400 µm,
a $d50_{,3}$-value in the range of 400 to 750 µm and
a $d90_{,3}$-value in the range of 800 to 1200 µm.

In each case on condition that the $d10_{,3}$-value is lower than the $d50_{,3}$-value and the $d50_{,3}$-value is lower than the $d90_{,3}$-value.

In the context of the present invention the "$d10_{,3}$-value", "$d50_{,3}$-value", and "$d90_{,3}$-value" describe the particle sizes based on the volume of the particles.

In the context of the present invention, the "$d10_{,3}$-value" is understood to mean the particle size at which 10% by volume of the particles, preferably the crystals (C), based on the total volume of the particles, preferably the crystals (C), are smaller than or equal to the $d10_{,3}$-value and 90% by volume of the particles, preferably the crystals (C), based on the total volume of the particles, preferably the crystals (C), are larger than the $d10_{,3}$-value. By analogy, "$d50_{,3}$-value" is understood to mean the particle size at which 50% by volume of the particles, preferably the crystals (C), based on the total volume of the particles, preferably the crystals (C), are smaller than or equal to the $d50_{,3}$-value and 50% by volume of the particles, preferably the crystals (C), based on the total volume of the particles, preferably the crystals (C), are larger than the $d50_{,3}$-value. Correspondingly, the "$d90_{,3}$-value" is understood to mean the particle size at which 90% by volume of the particles, preferably the crystals (C), based on the total volume of the particles, preferably the crystals (C), are smaller than or equal to $d90_{,3}$-value and 10% by volume of the particles, preferably the crystals (C), based on the total volume of the particles, preferably the crystals (C), are larger than $d90_{,3}$-value.

The particle sizes of the crystals (C) comprised in the crystal composition (CC), the $d10_{,3}$-values, the $d50_{,3}$-values and the $d90_{,3}$-values, as well as the average aspect ratios ($b/I_3$), the average sphericity ($SPTH_3$), the average $X_{c\ min}$ diameter and the average maximum Feret diameter ($X_{Fe\ max}$) are determined with a Camsizer® XT (of the company Retsch Technology) using the measuring methods described in the manual "CAMSIZER® Characteristics, Basics of definition DIN 66141, Retsch Technology dated Nov. 5, 2009."

The particle sizes (hereinafter the wording "particle size" and "particle diameter" are used synonymously and have the same meaning) are determined on basis of definition DIN 66141 dated February 1974. Therefore, the crystal composition (CC) is fed via a vibrating feeder past the measurement optic of the Camsizer® XT at room temperature (20° C.) and normal pressure (1.01325 bar), wherein at least 80 000 particles, preferably crystals (C), are measured.

The $d10_{,3}$-values, the $d50_{,3}$-values and the $d90_{,3}$-values are determined by the $X_{area}$ method. With the measuring method $X_{area}$ the particle diameter is calculated by the area of particle projection using the following formula:

$$X_{area} = \sqrt{\frac{4A}{\pi}},$$

wherein the diameter of the area equivalent circle with a volume of a sphere with the diameter of $X_{area}$ is determined.

The bulk density of the crystal composition (CC) is generally in the range of 600 to 950 kg/m³, preferably in the range of 700 to 850 kg/m³ and more preferably in the range of 720 to 820 kg/m³. The bulk density of the crystal composition (CC) is determined according to EN ISO 60:2000-01; DIN 5 3 468.

The tappered density (measured after 1250 lifts) of the crystal composition (CC) is generally in the range of 700 to 1050 kg/m³, preferably in the range of 800 to 950 kg/m³ and more preferably in the range of 820 to 920 kg/m³. The tappered density of the crystal composition (CC) is determined according to DIN ISO 787 part 11 (after 1250 lifts).

The Hausner ratio of the crystal composition (CC) is generally in the range of 1.05 to 1.27, preferably in the range of 1.08 to 1.25 and more preferably in the range of 1.1 to 1.2.

The Hausner ratio is the ratio of tappered density to bulk density. The Hausner ratio is a parameter for the flowability of particulate compositions, wherein the flowability is classified according to the following table:

| Hausner ratio | Flowability |
|---|---|
| 1.05-1.18 | Excellent |
| 1.14-1.19 | Good |
| 1.22-1.27 | Acceptable |
| 1.3-1.54 | Poor |
| 1.49-1.61 | Very Poor |
| >1.67 | Not Flowing |

Another object of the present invention, therefore, is a crystal composition (CC), wherein the Hausner ratio is in the range of 1.05 to 1.27.

The crystal composition (CC) preferably has a flowability ($ff_c$) according to Jenike and ASTM-D 6773 at an initial shear stress of 3 kPa in the range of 7 to 50, preferably in the range of 8 to 40, more preferably in the range of 8.5 to 20 and particularly preferred in the range of 9 to 15.

According to Jenike the flowability is classified according the following table:

| $ff_c$ | Flowability |
|---|---|
| <1 | Not flowing |
| 1 < to <2 | Very poor |
| 2 < to <4 | Poor |
| 4 < to <10 | Good |
| 10 < | Excellent |

The crystals (C) contained in the crystal composition (CC) according to the invention generally have an average aspect ratio in the range of 0.2 to 1, preferably in the range of 0.3 to 0.8, more preferably in the range of 0.4 to 0.7 and particularly preferred in the range of 0.5 to 0.65.

The average aspect ratio of the crystals (C) comprised in the crystal composition (CC) is determined with a Camsizer® XT using the method $b/I_3$ as described in the above referenced manual on basis of definition DIN 66141 dated February 1974. The aspect ratio is calculated by using the following formula:

$$b/l_3 = \frac{X_{cmin}}{X_{Femax}}$$

$X_{c\ min}$ is the volume average particle diameter which is the shortest cort of the measured set of maximum corts of the particle projection (the crystal (C) projection).

FIG. 8 shows an example, how $X_{c\ min}$ is measured. $X_{c\ min}$ is the volume average of the shortest cort over all particles (crystals (C)), comprised in the crystal composition (CC).

The maximum feret diameter ($X_{Fe\ max}$) is the volume average particle diameter over all particles (crystals (C)), comprised in the crystal composition (CC), which is the longest ferret diameter of the measured set of feret diameter of a particle. The determination of the maximum feret diameter $x_{Fe}$ max is shown by the way of example in FIG. 8.

The crystals (C) contained in the crystal composition (CC) according to the invention have generally an average sphericity ($SPHT_3$) in the range of 0.75 to 0.85, preferably in the range of 0.76 to 0.82 and more preferably in the range of 0.77 to 0.81. The sphericity is measured according to ISO 9276-6:2012-1.

Therefore, another object of the present invention is a crystal composition (CC), wherein the average sphericity of the crystals (C) is in the range of 0.75 to 0.85.

The crystal composition (CC) has generally an APHA-color number (ASTM D1209) in the range of 10 to 120, preferably in the range of 15 to 100, more preferably in the range of 20 to 80. The APHA-color numbers were measured on a Hach Lange LICO 500 instrument; 2.5 g 4,4'-DCDPSO (4,4'-DCDPSO=4,4'dichlorodiphenylsulfoxide) were dissolved in 20 ml NMP and measured against pure NMP (NMP=N-Methyl-2-pyrrolidone).

Crystal (C)

Another object of the present invention is a crystal (C) consisting of
(a) at least 95% by weight 4,4'-dichlorodiphenylsulfoxide,
(b) 0 to 2% by weight of impurities and
(c) 0 to 3% by weight of an organic solvent (os),
based in each case on the total weight of the crystal (C), wherein the outer surface of the crystal (C) comprises
i) a six-sided base surface (bsu) and
ii) a six-sided top surface (tsu) and
iii) six side surfaces (ssu1 to ssu6), joining the corresponding sides of the six-sided base surface (bsu) and the six-sided top surface (tsu).

The crystal (C) can differ from the crystals (C) comprised in the crystal composition (CC). In a preferred embodiment, the crystal (C) does not differ from the crystals (C) comprised in the crystal composition (CC). In a preferred embodiment, therefore, the features and preferences mentioned above in a view of the crystal composition (CC) apply for the crystal (C) accordingly. In another preferred embodiment, therefore, the features and preferences mentioned hereinafter in view of the crystal (C) apply for the crystal composition (CC) accordingly.

Another object of the present invention, therefore, is a crystal composition (CC) comprising crystals (C), wherein the crystals (C) consist of
(a) at least 95% by weight of 4,4'-dichlorodiphenylsulfoxide,
(b) 0 to 2% by weight of impurities, and
(c) 0 to 3% by weight of an organic solvent (os),
based on the total weight of the crystals (C) contained in the crystal composition (CC), wherein the crystal composition (CC) has
a $d10_{,3}$-value in the range of 100 to 400 μm,
a $d50_{,3}$-value in the range of 300 to 800 μm and
a $d90_{,3}$-value in the range of 700 to 1500 μm,
wherein the $d10_{,3}$-value is lower than the $d50_{,3}$-value and the $d50_{,3}$-value is lower than the $d90_{,3}$-value, wherein the outer surface of the crystals (C) comprises
  i) a six-sided base surface (bsu) and
  ii) a six-sided top surface (tsu) and
  iii) six side surfaces (ssu1 to ssu6), joining the corresponding sides of the six-sided base surface (bsu) and the six-sided top surface (tsu)

In a preferred embodiment the crystal (C) comprises at least 96% by weight, more preferably at least 97% by weight and most preferably at least 98% by weight of 4,4'-dichlorodiphenylsulfoxide, based in each case on the total weight of the crystal (C).

In a preferred embodiment the crystal (C) comprises from 0 to 1.5% by weight, more preferably from 0 to 1% by weight of impurities, based in each case on the total weight of the crystal (C).

In a preferred embodiment the crystal (C) comprises from 0 to 2.5% by weight, more preferably from 0 to 2% by weight, most preferably from 0 to 1% by weight and particularly preferred from 0 to 0.7% by weight of an organic solvent (os), based in each case on the total weight of the crystal (C).

Another object of the present invention is a crystal (C) wherein the impurities (b) comprise at least 90% by weight, preferably at least 95% by weight, more preferably at least 98% by weight and particularly preferred at least 99% by weight of one or more compounds selected from the group consisting of 2,4'-dichlorodiphenylsulfoxide, 3,4'-dichlorodiphenylsulfoxide, 2,2'-dichlorodiphenylsulfoxide, 4,4'-dichlorodiphenylsulfide, and one or more aluminum compounds, in each case based on the total weight of the impurities (b) contained in the crystal (C).

In another particularly preferred embodiment the impurities contained in the crystal (C) consist of one or more compounds selected from the group consisting of 2,4'-dichlorodiphenylsulfoxide, 3,4'-dichlorodiphenylsulfoxide, 2,2'-dichlorodiphenylsulfoxide, 4,4'-dichlorodiphenylsulfide, and one or more aluminum compounds.

The aluminum compounds optionally contained as impurities in the crystal (C) may be one or more compounds selected from the group consisting of $AlCl_3$, $Al(OH)Cl_2$, $Al(OH)_2Cl$, $Al(OH)_3$ and $AlO(OH)$.

The aluminum content in the crystal (C) is preferably in the range of 2 to 100 ppm by weight, more preferably in the range of 5 to 80 ppm by weight and most preferably in the range of 7 to 60 ppm by weight, in each case based on the total weight of the crystal (C). The aluminum content is determined as described below in the section examples.

Another preferred object of the present invention is a crystal (C) wherein the organic solvent (os) comprises at least 98% by weight of monochlorobenzene, based on the total weight of the organic solvent (os) contained in the crystal (C).

Another preferred object of the present invention is a crystal composition (CC), wherein the unit cell of the crystals (C) is monoclinic, space group C 2/m, cell lengths a=16.05 Å±0.05 Å, b=9.82 Å±0.05 Å, c=7.21 Å±0.05 Å, cell angles alpha 90°±0.1°, beta 95.7°±0.1°, gamma 90°±0.1°, and a cell volume 1131.5 Å$^3$±1 Å$^3$. In the present invention A means Angstrom and equals 0.1 nm.

The geometry of the outer surface of the crystal (C) is similar to a prism with a six-sided base surface and a six-sided top surface, wherein the jacket surface of the prism comprises six-side surfaces. FIG. 1A shows the net of a prism with a symmetrical six-sided base surface (bsu) and a symmetrical six-sided top surface (tsu) and six side surfaces (ssu1 to ssu6).

In a preferred embodiment the six-sided base surface (bsu), the six-sided top surface (tsu) and the six side surfaces (ssu1 to ssu6) account for at least 90% of the outer surface of the crystal (C). Another object of the present invention therefore, is a crystal (C), wherein the six-sided base surface (bsu), the six-sided top surface (tsu) and the six side surfaces (ssu1 to ssu6) account for at least 90% of the outer surface of the crystal (C).

In a preferred embodiment the six-sided base surface (bsu), the six-sided top surface (tsu) and the six-side surface (ssu1 to ssu6) account for at least 92% of the outer surface of the crystal (C).

The crystal (C) according to the present invention may contain further surfaces for example irregularities or intergrowth. Generally the further surfaces of the crystal (C) according to the invention account for 0 to at most 10%, preferably from 0 to at most 8% of the outer surface of the crystal (C).

Another preferred object of the present invention is a crystal (C), wherein the diameter (db) of the six-sided base surface (bsu) and the diameter (dt) of the six-sided top surface (tsu) are each independently in the range of 50 to 1500 μm, preferably in the range of 100 to 1200 μm.

Another preferred object of the present invention is a crystal (C), wherein the length (l1) of the first side surface (ssu1), the length (l2) of the second side surface (ssu2), the length (l3) of the third side surface (ssu3), the length (l4) of the fourth side surface (ssu4), the length (l5) of the fifth side surface (ssu5) and the length (l6) of the sixth side surface (ssu6) are each independently in the range of 100 to 3000 μm, preferably in the range of 200 to 2500 μm.

The six-sided top surface (tsu) and the six-sided base surface (bsu) may be symmetrical or asymmetrical. If the six-sided top surface (tsu) and the six-sided base surface (bsu) are symmetrical the six sides (tsi1 to tsi6) of the six-sided top surface (tsu) as well as the six sides (bsi1 to bsi6) of the base surface (bsu) have the same length. In this case the distance (dt14) between the first corner (ct1) and the fourth corner (ct4) as well as the distance (dt36) between the third corner (ct3) and the sixth corner (ct6) and the distance (dt25) between the second corner (ct2) and the fifth corner (ct5) of the top surface (tsu) have all the same length. If the base surface (bsu) is symmetrical, the distances (db14), (db25) and (db36) also have the same length. Therefore, for a symmetrical top surface (tsu) the diameter (dt) equals the distances (dt14), (dt25) and (dt36). For a symmetrical base surface (bsu) the diameter (db) equals the distances (db14), (db25) and (db36).

In case the crystal (C) has an asymmetrical base surface (bsu) and/or an asymmetrical top surface (tsu) the diameter (db) of the six-sided base surface (bsu) in a preferred embodiment is the average of the distances (db14), (db25) and (db36). The distance (db14) is the shortest distance between the first corner (cb1) and the fourth corner (cb4) of the six-sided base surface (bsu) of the crystal (C). The distance (db25) is the shortest distance between the second corner (cb2) and the fifth corner (cb5) and the distance (db36) is the shortest distance between the third corner (cb3) and the sixth corner (cb6) and the diameter (dt) of the six-sided top surface (tsu) in a preferred embodiment is the average of the distances (dt14), (dt25) and (dt6). The distance (dt14) is the shortest distance between the first corner (ct1) and the fourth corner (ct4) of the six-sided top surface (tsu) of the crystal (C). The distance (dt25) is the shortest distance between the second corner (ct2) and the fifth corner (ct5) and the distance (dt36) is the shortest distance between the third corner (ct3) and the sixth corner (ct6), as illustrated by example in FIG. 1B.

The side surfaces (ssu1 to ssu6) independently of each other may have essentially the form of a square, a rectangle, a rhombus, a kite, a parallelogram, an isosceles trapezium or an irregular quadrilateral. In case the side surfaces (ssu1 to ssu6) have an asymmetrical form, the lengths (l1 to l6) of the side surfaces (ssu1 to ssu6) are preferably determined as follows. As illustrated in FIG. 1C the length (l1) of the first side surface (ssu1) is the average of the shortest distance (l11) between the first corner (ct1) of the top surface (tsu) and first corner (bt1) of the base surface (btu) and the shortest distance (l22) between the second corner (ct2) of the top surface (tsu) and the second corner (bt2) of the second corner (bt2) of the base surface (bsu). Accordingly, in this case the length (l2) of the second side surface (ssu2) is the average of the shortest distance (l22) between the second corner (ct2) of the top surface (tsu) and the second corner (bt2) of the second corner (bt2) of the base surface (bsu) and the shortest distance (l33) between the third corner (ct3) of the top surface (tsu) and third corner (bt3) of the base surface (btu).

The lengths (l3 to l6) are determined accordingly.

The term "have essentially the form of a square, a rectangle, a rhombus, a kite, a parallelogram, an isosceles trapezium or an irregular quadrilateral" according to the present invention may be defined as follows: "have essentially the form of a square, a rectangle, a rhombus, a kite, a parallelogram, an isosceles trapezium or an irregular quadrilateral" defines that the side surfaces (ss1 to ss6) of the crystal (C) occupy at least 80%, preferred at least 85%, more preferred at least 90%, and particularly preferred 50% of the interior surface of a hypothetical best fit of a square, a rectangle, a rhombus, a kite, a parallelogram, an isosceles trapezium or an irregular quadrilateral in which the side surfaces (ss1 to ss6) of the crystal (C) fit.

The dimensions of the crystal (C) are preferably measured using light microscopy.

The crystal composition (CC) according to the present invention can be produced by a process comprising the steps:

I) cooling a first liquid mixture comprising 4,4'-dichlorodiphenylsulfoxide dissolved in an organic solvent (os) to obtain a suspension comprising crystallized 4,4'-dichlorodiphenylsulfoxide and the organic solvent (os), II) filtering the suspension obtained in step I) to obtain a filtrate comprising 4,4'-dichlorodiphenylsulfoxide dissolved in the organic solvent (os), wherein the filtrate has a lower concentration of 4,4'-dichlorodiphenylsulfoxide compared to the first liquid mixture, and a filter residue comprising the crystallized 4,4'-dichlorodiphenylsulfoxide, III) concentrating the filtrate obtained in step II) to obtain a second liquid mixture, wherein the second liquid mixture has a higher concentration of 4,4'-dichlorodiphenylsulfoxide compared to the filtrate, IV) recycling at least a part of the second liquid mixture obtained in step III) into step I), and V) drying the filter residue obtained in step II) to obtain the crystal composition (CC).

In a preferred embodiment the filter residue obtained in step II) is washed with an organic solvent (os), preferably monochlorobenzene, before drying according to step V). The washing filtrate is preferably also recycled to the concentrating step III).

The crystal (C) according to the present invention can be produced by a process comprising the step:

VI) separating a crystal (C) out of the crystal composition (CC) obtained in step V).

Another object of the present invention, therefore, is a crystal composition (CC) obtained by a process comprising the steps:

I) cooling a first liquid mixture comprising 4,4'-dichlorodiphenylsulfoxide dissolved in an organic solvent (os) to obtain a suspension comprising crystallized 4,4'-dichlorodiphenylsulfoxide and the organic solvent (os), II) filtering the suspension obtained in step I) to obtain a filtrate comprising 4,4'-dichlorodiphenylsulfoxide dissolved in the organic solvent (os), wherein the filtrate has a lower concentration of 4,4'-dichlorodiphenylsulfoxide compared to the first liquid mixture, and a filter residue comprising the crystallized 4,4'-dichlorodiphenylsulfoxide, III) concentrating the filtrate obtained in step II) to obtain a second liquid mixture, wherein the second liquid mixture has a higher concentration of 4,4'-dichlorodiphenylsulfoxide compared to the filtrate, IV) recycling at least a part of the second liquid mixture obtained in step III) into step I), and V) drying the filter residue obtained in step II) to obtain the crystal composition (CC).

And yet another object of the present invention is a crystal (C) obtained by a process comprising the step:

The organic solvent (os) used in the first liquid mixture can be any solvent in which 4,4'-dichlorodiphenylsulfoxide (DCDSPO) is sufficiently soluble in particular at a temperature suitable for industrial scale production and from which crystallized DCDPSO can be separated in a convenient manner. Such organic solvent (os) is for example chlorobenzene, toluene, xylene, mesitylene, methanol or a mixture of two or more of said solvents. The organic solvent (os) preferably is chlorobenzene, particularly monochlorobenzene.

Optionally for reducing the solubility of DCDPSO in the first liquid mixture and to improve the crystallization, it is possible to additionally add at least one drowning-out agent, for example at least one protic solvent like water, an alcohol, and/or an acid, particularly a carboxylic acid, or at least one highly unpolar solvent like a linear and/or cyclic alkane. With respect to ease of workup water, methanol, ethanol, acetic acid and/or formic acid, particularly water and/or methanol are preferred drowning-out agents.

VI) separating a crystal (C) out of the crystal composition (CC) obtained in step V).

The crystal composition (CC) can be used for the production of monomers, polymers and/or pharmaceuticals. If the crystal composition (CC) is used as a starting product or intermediate for the production of monomers, it is preferably used for the production of 4,4'-dichlordiphenylsulfone. Therefore, the 4,4'-dichlordiphenylsulfoxide is generally reacted with an oxidation agent in order to obtain the 4,4'-dichlordiphenylsulfone. As an oxidation agent, any oxidation agent can be used wherein organic peroxyacid is preferred.

In case the crystal composition (CC) is used as a starting product or intermediate for the production of polymers, it is preferably used for the production of polyarylene ether sulfone polymers, wherein polysulfone (PSU), polyethersulfone (PESU) and/or polybiphenylsulfone (PPSU) are particularly preferred.

If the crystal composition (CC) is used for the production of the above-mentioned preferred polyarylene ether sulfone polymers, it is typically reacted, as mentioned above, with an oxidation agent to obtain 4,4'-dichlordiphenylsulfone. The 4,4'-dichlordiphenylsulfone is generally subsequently reacted with an aromatic dihydroxymonomer in order to obtain the above-mentioned polyarylene ether sulfone polymers.

For the production of polysulfone (PSU), the 4,4'-dichlordiphenylsulfone is generally reacted with bisphenol A (4,4'-(propane-2,2-diyl)diphenol). In order to obtain polyethersulfone (PESU), the 4,4'-dichlorodiphenylsulfone is generally reacted with 4,4'-dihydroxydiphenylsulfone. In order to obtain polybiphenylsulfone (PPSU), the 4,4'-dichlordiphenylsulfone is generally reacted with 4,4'-dihydroxybiphenyl.

Another object of the present invention, therefore, is the use of the crystal composition (CC) as an intermediate for the production of at least one product selected from the group consisting of monomers, polymers and pharmaceuticals.

The invention is described in more detail by the examples hereinafter without being restricted thereto.

EXAMPLES

Production of the Crystal Composition (CC)/the Crystal (C) According to the Invention For the production of 4,4'-dichlorodiphenylsulfoxide (DCDPSO) 5.5 mol aluminum chloride and 40 mol monochlorobenzene (MCB) were fed into a stirred tank reactor as a first reactor. Subsequently 5 mol thionyl chloride were added into the first reactor within 160 minutes. The reaction in the first reactor was carried out at a temperature of 10° C. The hydrogen chloride produced during the reaction was withdrawn from the first reactor. After finishing the addition of thionyl chloride the reaction mixture in the first reactor was heated to 60° C.

After completion of the reaction in the first reactor, the resulting reaction mixture was fed into a stirred tank reactor as a second reactor containing 3400 g aqueous hydrochloric acid with a concentration of 11% by weight. The second reactor was heated to a temperature of 90° C. with stirring. After 30 minutes the stirring was stopped and the mixture contained in the second reactor separated into an aqueous phase and in organic phase. The aqueous phase was withdrawn.

The organic phase was washed with 3000 g water while stirring at 90° C. After washing, the stirring was stopped and the mixture separated into an aqueous phase and in organic phase. The aqueous phase was removed. The organic phase was subjected to a distillation.

Monchlorobenzene was distilled from said organic phase until saturation is reached. The distillation was carried out at a temperature of 88 to 90° C. at a pressure of 200 mbar (abs). The saturation was monitored via a turbidity probe.

Subsequently an evaporation cooling crystallization was performed with the saturated organic phase containing monochlorobenzene and 4,4'-dichlorodiphenylsulfoxide obtained in the above described distillation (equals cooling step I) of the present invention) until the temperature reached 20° C. Therefore, the organic phase was refluxed due to pressure reduction and simultaneously cooled by the condensed liquid. The pressure at the end of the evaporation cooling process is normally about 20 mbar (abs). After the evaporation cooling crystallization a suspension was obtained comprising a crystallized 4,4'-dichlorodiphenylsulfoxide and monochlorobenzene.

According to step II) of the present invention the suspension obtained in step I) was filtered to obtain a filtrate comprising 4,4'-dichlorodiphenylsulfoxide dissolved in monochlorobenzene and a filter residue comprising the crystallized 4,4'-dichlorodiphenylsulfoxide. The filter residue was washed with monochlorobenzene and subsequently dried at 100° C. and 100 mbar (abs) in order to obtain the crystal composition (CC) (equals step V) of the present invention).

According to step III) the washing filtrate and the filtrate obtained in step II) were subjected to a distillation. In the distillation monochlorobenzene was removed until the amount of combined filtrate and washing filtrate was reduced to 25% by weight. The distillation was operated at 90° C. sump temperature and 200 mbar (abs). The distilled monochlorobenzene was reused in the next batch as starting material. 80% by weight of the obtained bottom product (equals second liquid mixture according to step III) of the present invention) were recycled into the crystallization step of the next batch (equals the cooling step I) according to the present invention).

The crystal composition (CC) was obtained in a steady state yield of 1232 g per batch which corresponds to a yield of 91.3%.

4,4'-dichlorodiphenylsulfoxide obtained from commercial suppliers:
abcr-DCDPSO: 4,4'-dichlorodiphenylsulfoxide obtained from abcr GmbH
Alfa-DCDPSO: 4,4'-dichlorodiphenylsulfoxide obtained from Alfa-Aesar
TCI-DCDPSO: 4,4'-dichlorodiphenylsulfoxide obtained from TCI GmbH
Recryst-DCDPSO: 4,4'-dichlorodiphenylsulfoxide recrystallized from diethylether
Recryst-DCDPSO; $CHCl_3$: 4,4'-dichlorodiphenylsulfoxide recrystallized from chloroform
Recryst-DCDPSO; EA: 4,4'-dichlorodiphenylsulfoxide recrystallized from ethyl acetate Analytical Methods The $d10_{,3}$-values, the $d50_{,3}$-values and the $d90_{,3}$-values are determined as described above using a Camsizer®XT with a measuring method $x_{area}$.

GC analysis was performed to determine any organic impurity, solvent and the purity of the 4,4'-dichlorodiphenylsulfoxide. Samples were diluted in dimethylformamide (DMF) and the internal standard tridecane was added to quantify the components based on calibration curves. GC analysis was performed using a RTx5 Amine column (0.25 µm) from Restek® using the following temperature ramp: holding 50° C. for 2 minutes, heating 15° C. per minute until 250° C. is reached, holding 250° C. for 15 minutes.

APHA numbers were measured (as described above) on a Hach Lange LICO 500 instrument; 2.5 g 4,4'-dichlorodiphenylsulfoxide were dissolved in 20 mL N-methyl-2-pyrrolidone (NMP) and measured against pure NMP.

Determination of the aluminum content was done by generating a saturated solution of 4,4'-dichlorodiphenylsulfoxide in dimethylformamide to generate a homogeneous solution. Subsequently, a sample of said saturated solution was taken and the weight was determined (100 to 200 mg+/−0.1 mg). Afterwards, the following decomposition process was conducted. 8 ml of concentrated sulfuric acid (96% w/w) were added to the sample and heated to 320° C. Subsequently, 7 ml of a mixed acid ($H_2SO_4$ 96% w/w; $HClO_4$ 70% w/w; $HNO_3$ 65% w/w in a volume ratio 2:1:1) were added and the sample as then heated to 160° C. Thereafter, the excess acid was evaporated. Subsequently 12 ml of hydrochloric acid (HCl 36% w/w) were added and the mixture was heated to reflux to obtain a solution. The exact volume of said solution was determined by back weighting and correction with the density. Thereafter, the aluminum content of the solution was measured by inductively coupled optical plasma emission spectroscopy. (Instrument IPC-OES Agilent 5100; wave length Al 394, 401 nm; internal standard SC 361.383 nm)

Bulk density and tapered density were determined as described above.

The flowability ($ff_c$) was determined on a Ring Shear Tester RST-XS according to Jenike as described in Dr.-Ing. Dietmar Schulze "*The automatic Ring Shear Tester RST-01.pc*" and ASTM-D 6773 at an initial shear stress of 3 kPa.

According to Jenike the flowability is classified according the following table:

| $ff_c$ | Flowability |
|---|---|
| <1 | Not flowing |
| 1 < to <2 | Very poor |
| 2 < to <4 | Poor |
| 4 < to <10 | Good |
| 10 < | Excellent |

The melting point was determined by DSC (Differential Scanning calorimetry) on a Mettler Toledo DSC3 using a heating rate of 2.5 K/min (30 to 410° C.).

The results are shown in the below table.

| | Color | Purity [wt.-%] | Impurities [wt.-%] | MCB [wt.-%] | Al content [ppm] | Particle size [µm] | APHA number | Bulk density [kg/m³] | Tapered bulk density (1250 lifts) [kg/m³] | Hausner ratio | Flowability [ffc] | Melting point [° C.] |
|---|---|---|---|---|---|---|---|---|---|---|---|---|
| abcr-DCDPSO | yellow powder | 99.1 | 4,4'-dichlorodiphenylsulfide 0.17<br>2,4'-dichlorodiphenylsulfoxide 0.17 | | n.d. | 960 | $d10_{,3}$ = 17<br>$d50_{,3}$ = 31<br>$d90_{,3}$ = 62 | >4000 | n.d. | n.d. | n.d. | 6.5 ± 0.4 | 141.4-142.5 |
| TCI-DCDPSO | white crystals | 99.1 | 2,4'-dichlorodiphenylsulfoxide | 0.20 | n.d. | <60 | $d10_{,3}$ = 53<br>$d50_{,3}$ = 491<br>$d90_{,3}$ = 1063 | 472 | n.d. | n.d. | n.d. | 5.8 ± 0.6 | 141.9-143.6 |
| Alfa-DCDPSO | white powder | 97.4 | 4,4'-dichlorodiphenylsulfide 0.26<br>2,4'-dichlorodiphenylsulfoxide 1.28 | | 1.12 | <60 | $d10_{,3}$ = 46<br>$d50_{,3}$ = 328<br>$d903$ = 1027 | 1420 | n.d. | n.d. | n.d. | n.d. | 140.9-143.1 |
| Recryst-DCDPSO | white powder | 99.9 | 2,4'-dichlorodiphenylsulfoxide | 0.1. | n.d. | <50 | $d10_{,3}$ = 29<br>$d50_{,3}$ = 55<br>$d90_{,3}$ = 1415 | 68. | n.d. | n.d. | n.d. | 6.6 ± 0.4 | 143.3-144.6 |

-continued

| | Color | Purity [wt.-%] | Impurities [wt.-%] | | MCB [wt.-%] | Al content [ppm] | Particle size [μm] | APHA number | Bulk density [kg/m³] | Tapered bulk density (1250 lifts) [kg/m³] | Hausner ratio | Flow-ability [ttc] | Melting point [° C.] |
|---|---|---|---|---|---|---|---|---|---|---|---|---|---|
| CC-DCDPSO according to the invention | white crystals | 98.8 | 4,4'-dichlorodi-phenylsulfide 2,4'-dichlorodi-phenylsulfoxide | 0.2 0.3 | 0.50 | <50 | $d10_{,3} = 231$ $d50_{,3} = 497$ $d90_{,3} = 863$ | 72 | 763 | 874 | 1.13 | 9.6 ± 0.4 | 141.2-144.9 |
| Recryst-DCDPSO CHCl₃ | white crystals | n.d. | n.d. | | n.d. | n.d. | n.d. | n.d. | n.d. | n.d. | n.d. | n.d. | 142.8-144.1 |
| Recryst-DCDPSOEA | white cystals | n.d. | n.d. | | n.d. | n.d. | n.d. | n.d. | n.d. | n.d. | n.d. | n.d. | 141.9-143.6 |

FIGURES AND REFERENCE SIGN LIST

FIG. 1A shows the net of a prism with a symmetrical six-sided base surface bsu and a symmetrical six-sided top surface tsu and six side surfaces ssu1 to ssu6

FIG. 1B shows the top view of the top surface tsu of an asymmetrical prism with a six-sided top surface tsu FIG. 1C shows the first side surface ssu of an asymmetrical six-sided prism FIG. 1D shows one embodiment of the geometry of the outer surface of the crystal C according to the invention FIG. 2A shows another embodiment of the geometry of the outer surface of the crystal C according to the invention FIG. 2B shows a photo taken with a light microscope of the geometry of the outer surface of the crystal C according to the invention with marked up edges and reference signs FIG. 3A shows a photo taken with a light microscope of the crystal composition CC showing crystals C (500 μm)

Figure 1D:
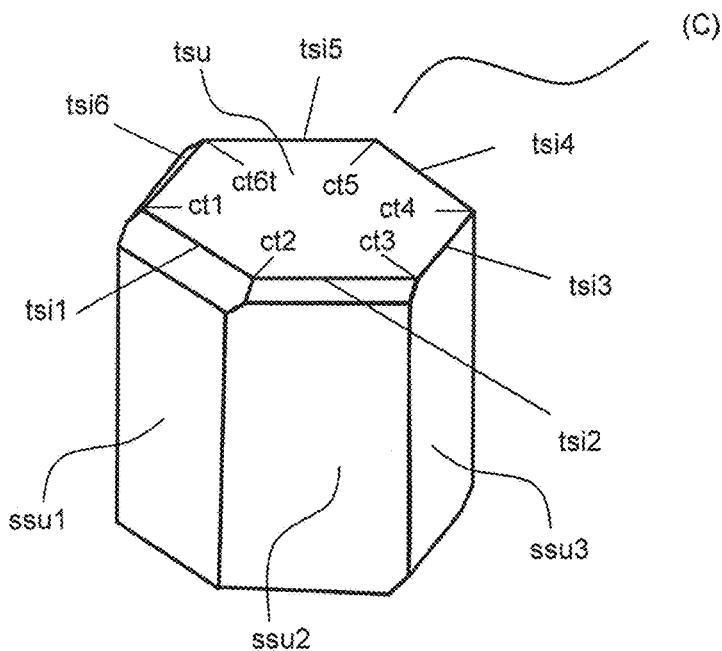
Figure 2A:
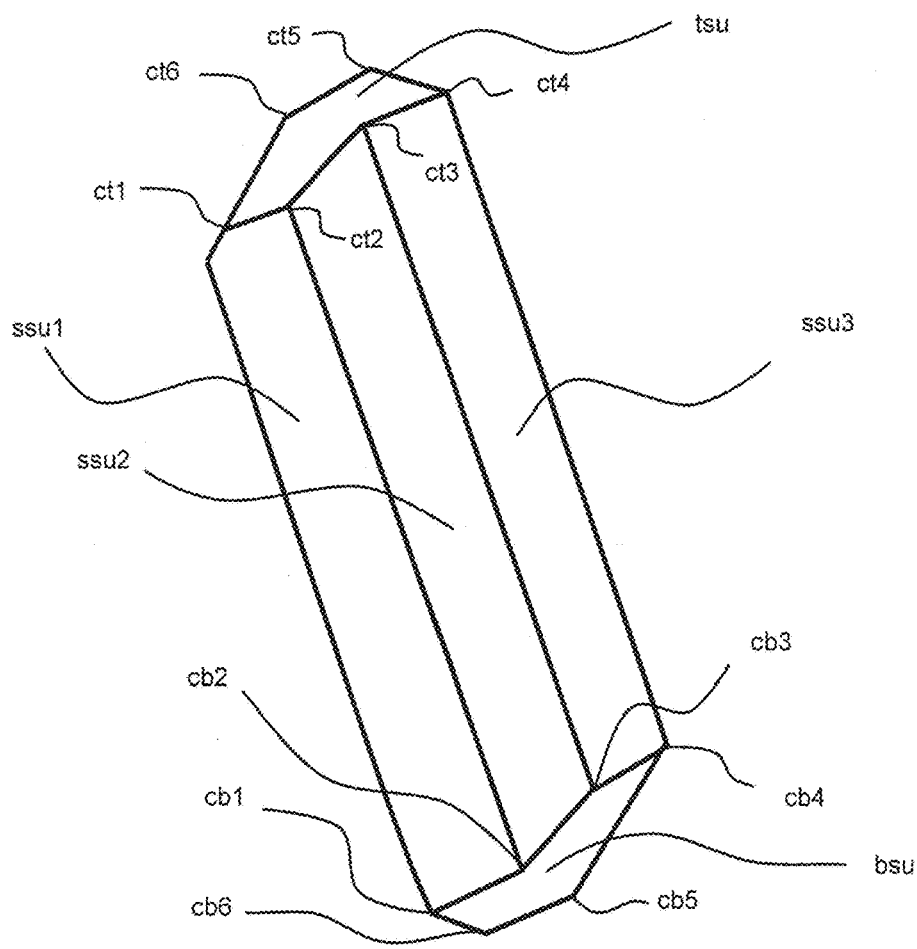
Figure 2B:
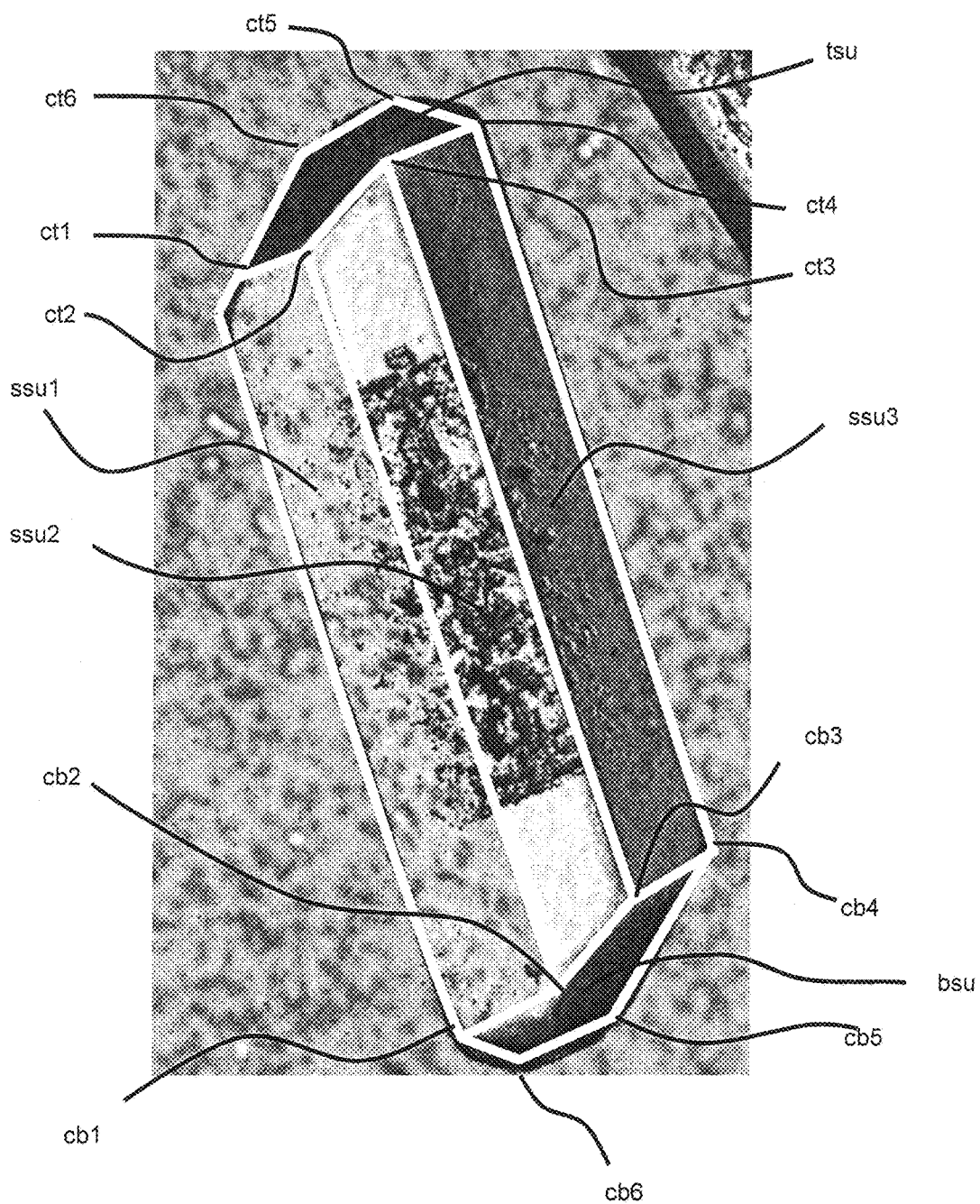
Figure 3A:
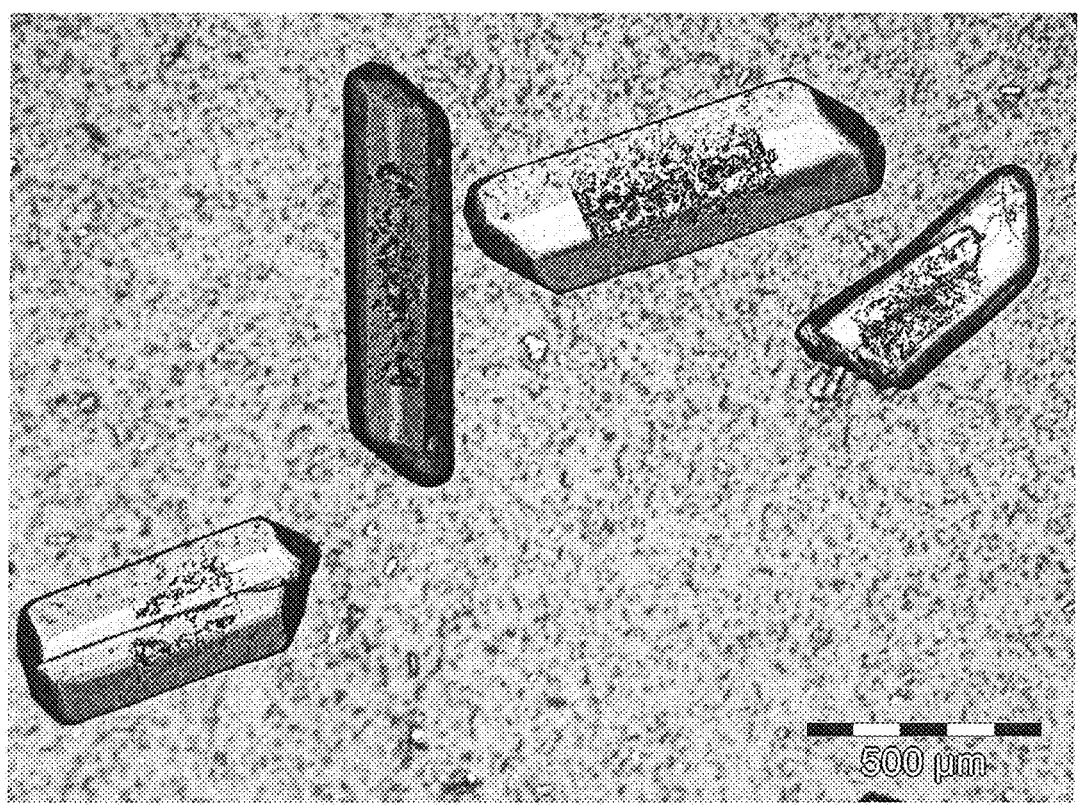
FIG. 3B shows a photo taken with a light microscope of the crystal composition CC showing crystals C (200 μm)
Figure 3B:
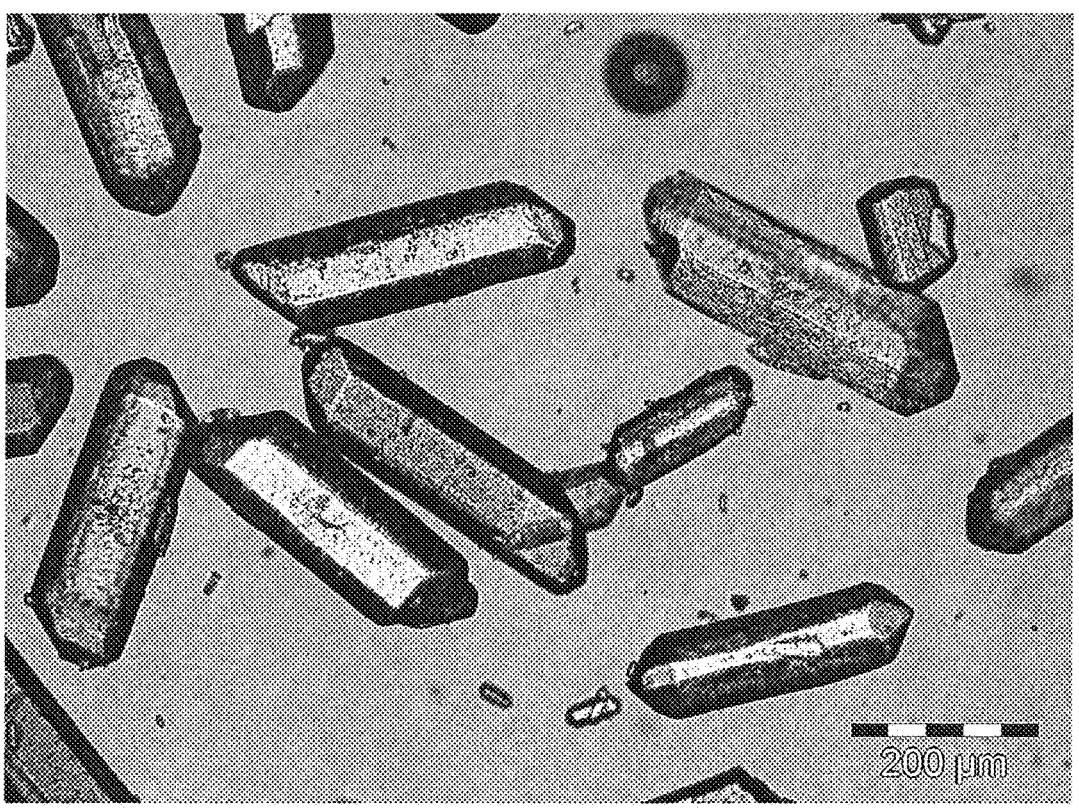
Figure 4A:
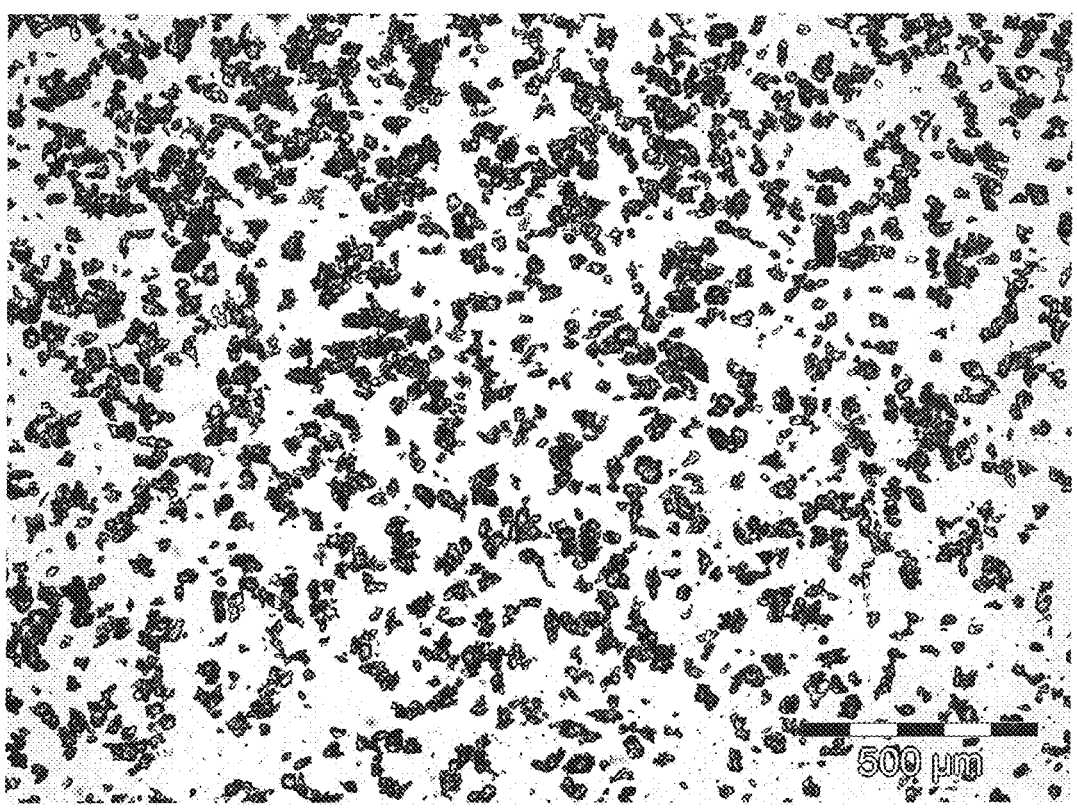
FIG. 4A shows a photo taken with a light microscope of 4,4'-dichlorodiphenylsulfoxide in particulate powder form obtained from abcr GmbH (500 μm)
Figure 4B:
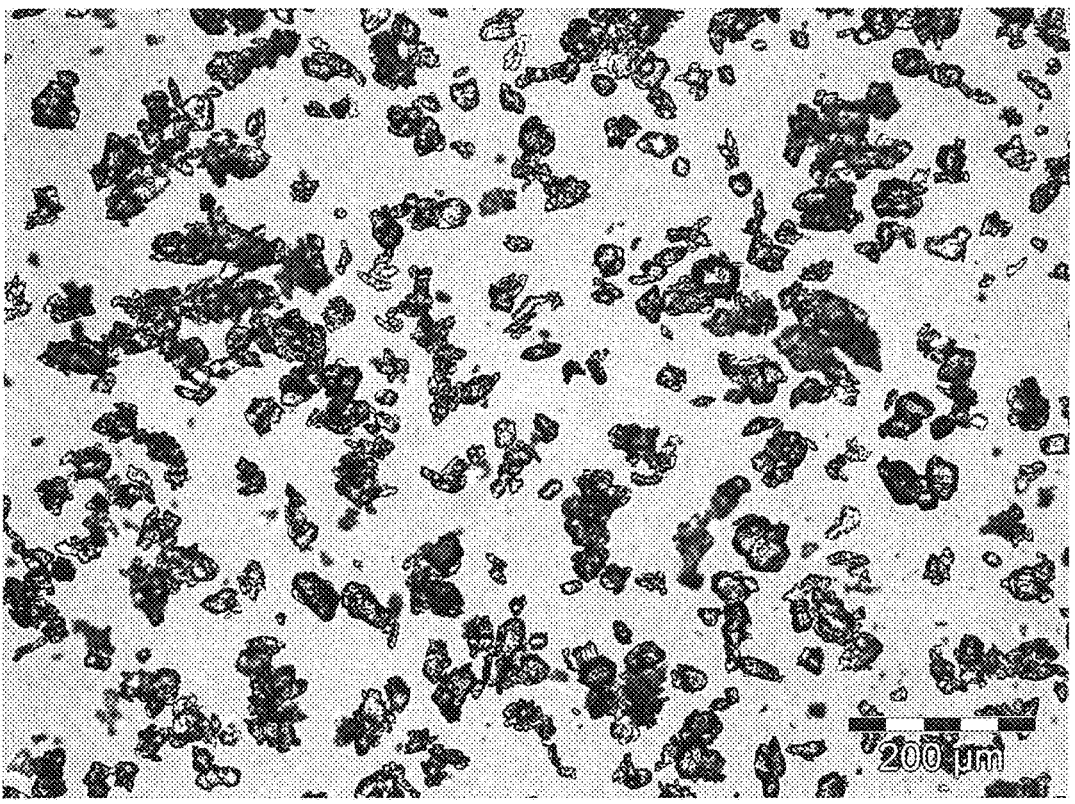
FIG. 4B shows a photo taken with a light microscope of 4,4'-dichlorodiphenylsulfoxide in particulate powder form obtained from abcr GmbH (200 μm)
Figure 5:
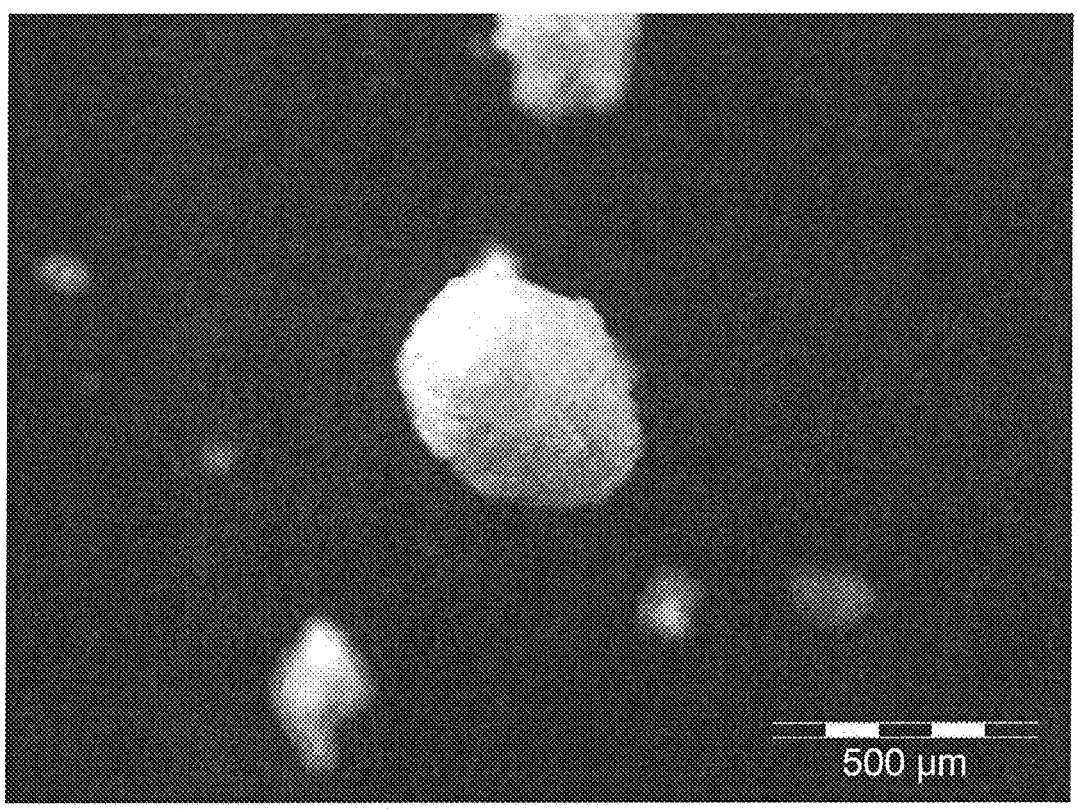
FIG. 5 shows a photo taken with a light microscope of 4,4'-dichlorodiphenylsulfoxide in particulate powder form obtained from Alfa Aesar (500 μm)
Figure 6A:
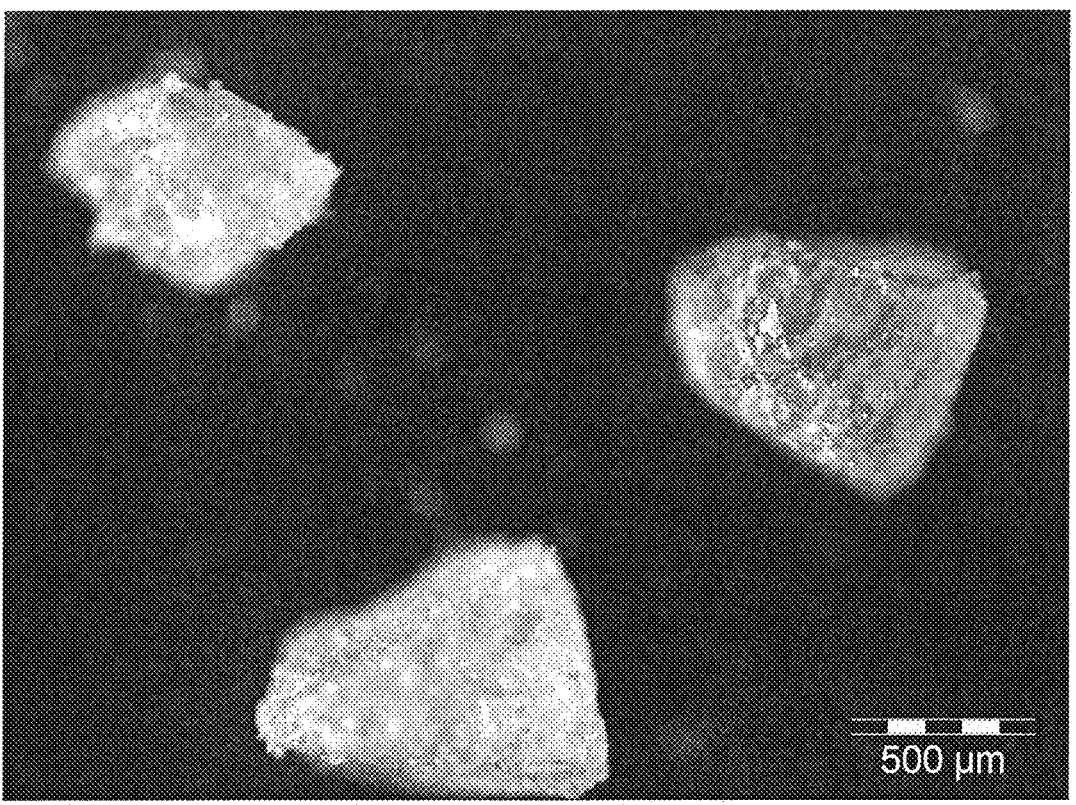
FIG. 6A shows a photo taken with a light microscope of 4,4'-dichlorodiphenylsulfoxide in particulate powder form obtained from TCI GmbH (500 μm)
Figure 6B:
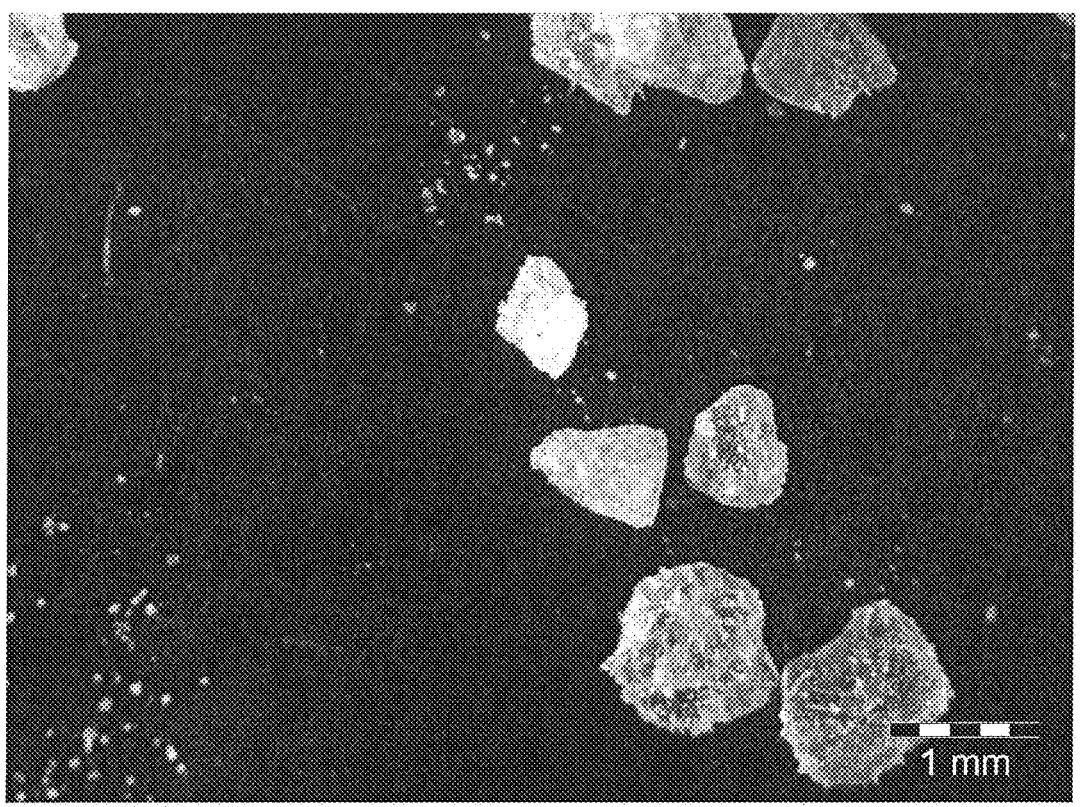
FIG. 6B shows a photo taken with a light microscope of 4,4'-dichlorodiphenylsulfoxide in particulate powder form obtained from TCI GmbH (1 mm)
Figure 7A:
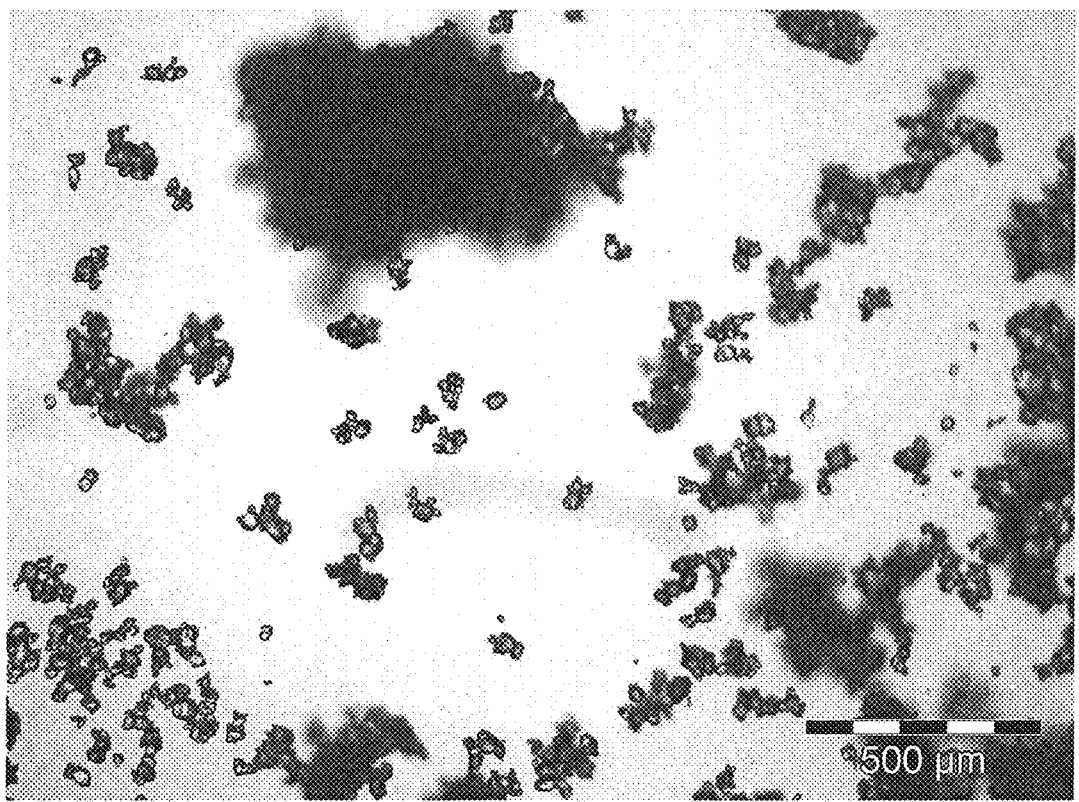
FIG. 7A shows a photo taken with a light microscope of 4,4'-dichlorodiphenylsulfoxide in particulate powder form recrystallized from diethyl ether (500 μm)
Figure 7B:
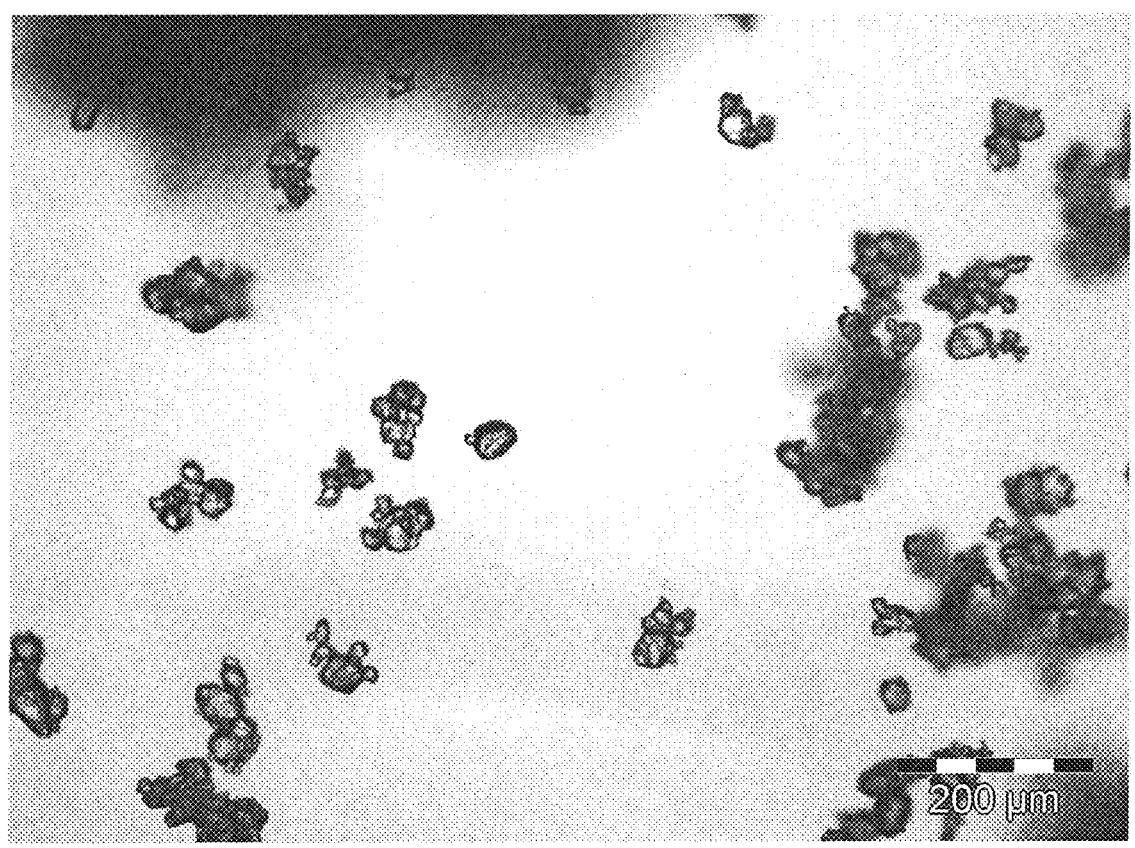
FIG. 7B shows a photo taken with a light microscope of 4,4'-dichlorodiphenylsulfoxide in particulate powder form recrystallized form diethylether (200 μm)
Figure 8A:
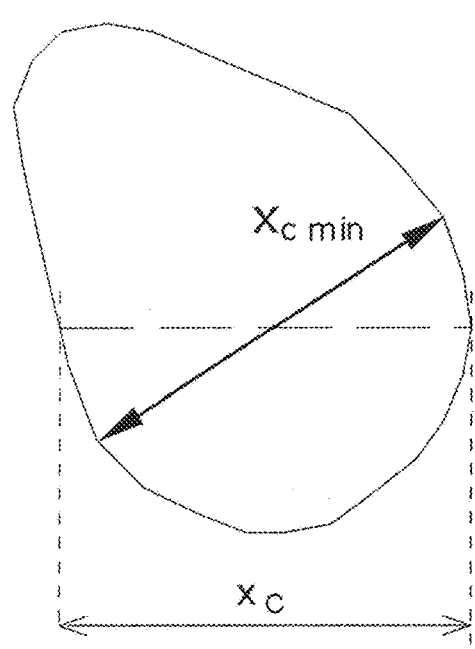
FIG. 8A illustrates the measurement of $X_{c\ min}$
Figure 8B:
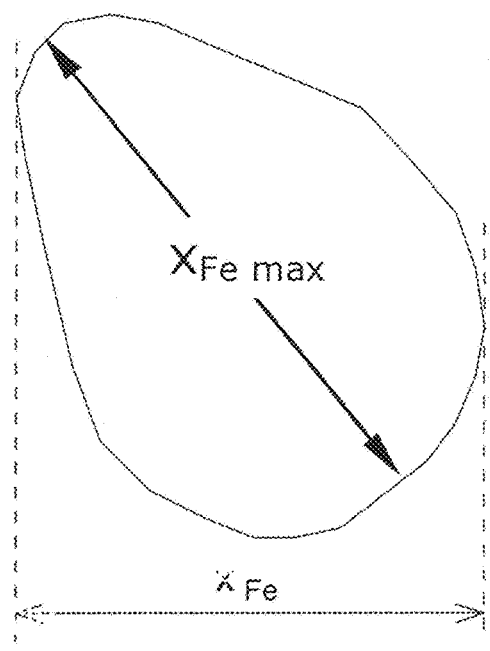
FIG. 8B illustrates the measurement of $X_{Fe\ max}$
Figure 9A:
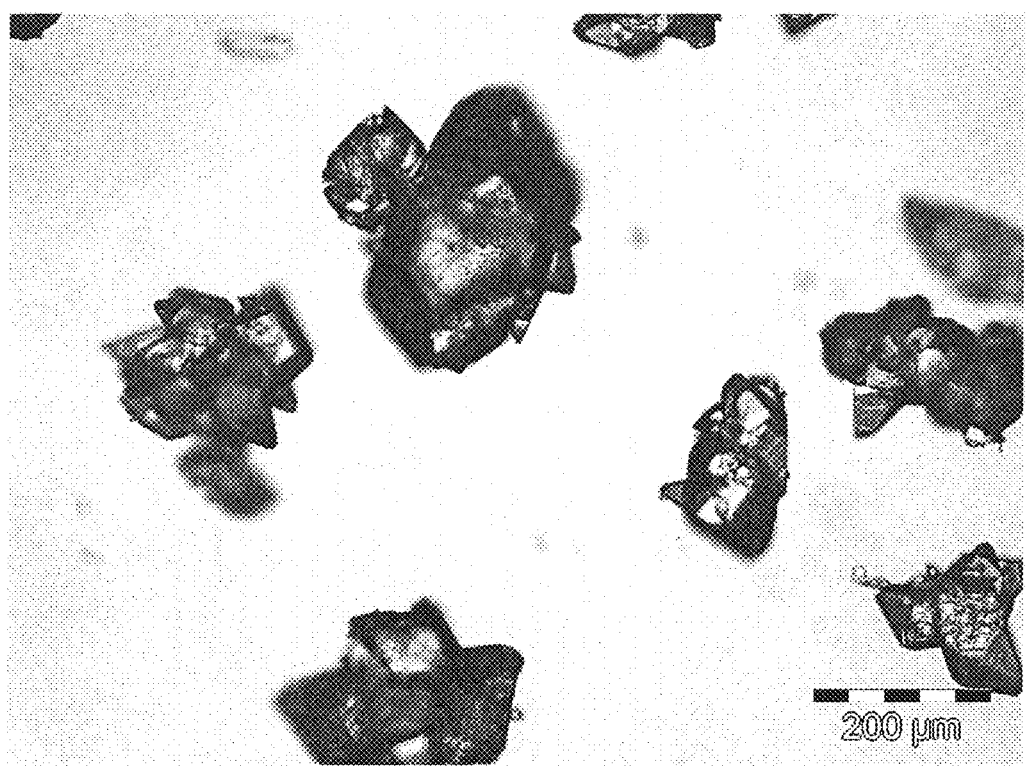
FIG. 9A shows a photo taken with a light microscope of 4,4'-dichlorodiphenylsulfoxide in particulate powder form recrystallized from chloroform (200 μm)
Figure 9B:
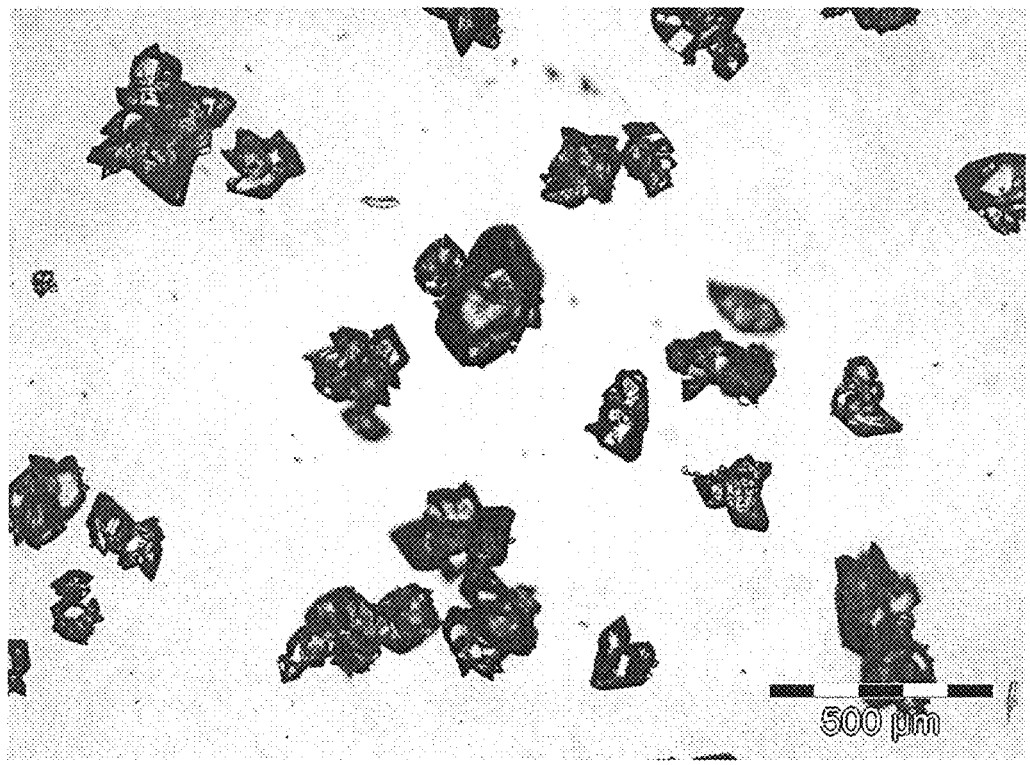
FIG. 9B shows a photo taken with a light microscope of 4,4'-dichlorodiphenylsulfoxide in particulate powder form recrystallized from chloroform (500 μm)
Figure 10:
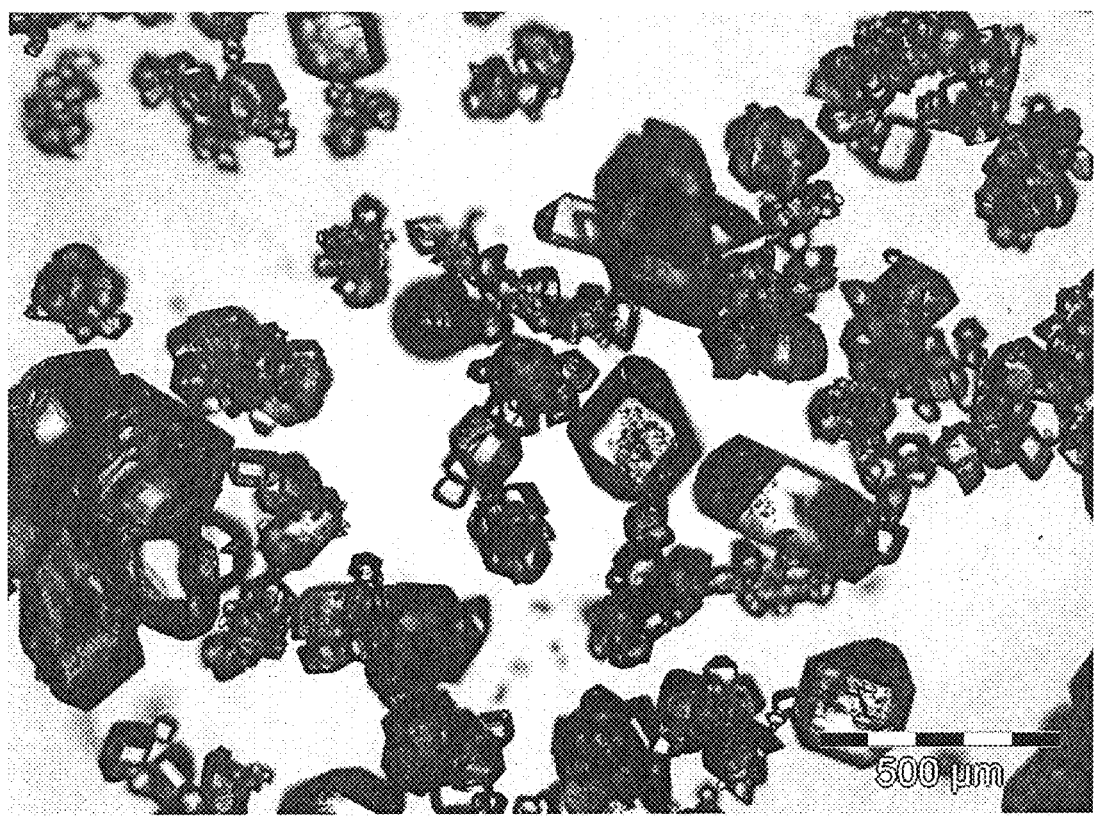

FIG. 10 shows a photo taken with a light microscope of 4,4'-dichlorodiphenylsulfoxide in particulate powder form recrystallized from ethyl acetate (500 μm)
C crystal
bsu six-sided base surface of the crystal (C)
bsi1 first side of the six-sided base surface bsu
bsi2 second side of the six-sided base surface bsu
bsi3 third side of the six-sided base surface bsu
bsi4 fourth side of the six-sided base surface bsu
bsi5 fifth side of the six-sided base surface bsu
bsi6 sixth side of the six-sided base surface bsu
cb1 first corner of the six-sided base surface bsu
cb2 second corner of the six-sided base surface bsu
cb3 third corner of the six-sided base surface bsu
cb4 fourth corner of the six-sided base surface bsu
cb5 fifth corner of the six-sided base surface bsu
cb6 sixth corner of the six-sided base surface bsu
db diameter of the six-sided base surface bsu
db14 shortest distance between the first corner cb1 and the fourth corner cb4
db25 shortest distance between the second corner cb2 and the fifth corner cb5
db36 shortest distance between the third corner cb3 and the sixth corner cb6
tsu six-sided top surface of the crystal C
tsi1 first side of the six-sided top surface tsu
tsi2 second side of the six-sided top surface tsu
tsi3 third side of the six-sided top surface tsu
tsi4 fourth side of the six-sided top surface tsu
tsi5 fifth side of the six-sided top surface tsu
tsi6 sixth side of the six-sided top surface tsu
ct1 first corner of the six-sided top surface tsu
ct2 second corner of the six-sided top surface tsu
ct3 third corner of the six-sided top surface tsu
ct4 fourth corner of the six-sided top surface tsu
ct5 fifth corner of the six-sided top surface tsu
ct6 sixth corner of the six-sided top surface tsu
dt diameter of the six-sided top surface tsu
dt14 shortest distance between the first corner ct1 and the fourth corner ct4
dt25 shortest distance between the second corner ct2 and the fifth corner ct5
dt36 shortest distance between the third corner ct3 and the sixth corner ct6
ssu1 first side surface of the crystal (C)
ssu2 second side surface of the crystal (C)
ssu3 third side surface of the crystal (C)
ssu4 fourth side surface of the crystal (C)
ssu5 fifth side surface of the crystal (C)

ssu6 sixth side surface of the crystal (C)
l1 length of the first side surface (ssu1)
l2 length of the second side surface (ssu2)
l3 length of the third side surface (ssu3)
l4 length of the fourth side surface (ssu4)
l5 length of the fifth side surface (ssu5)
l6 length of the sixth side surface (ssu6)
l11 shortest distance between the first corner ct1 and the first corner bt1
l22 shortest distance between the second corner ct2 and the second corner bt2
l33 shortest distance between the third corner ct3 and the third corner bt3
l44 shortest distance between the fourth corner ct4 and the fourth corner bt4
l55 shortest distance between the fifth corner ct5 and the fifth corner bt5
l66 shortest distance between the sixth corner ct6 and the sixth corner bt6

The invention claimed is:

1. A crystal composition (CC), comprising crystals (C), wherein the crystals (C) consist of
 (a) at least 95% by weight of 4,4'-dichlorodiphenylsulfoxide,
 (b) 0 to 2% by weight of impurities, and
 (c) 0 to 3% by weight of an organic solvent (os),
 based on a total weight of the crystals (C) comprised in the crystal composition (CC), wherein the crystal composition (CC) has
 a $d10_{,3}$-value in a range of 100 to 400 μm,
 a $d50_{,3}$-value in a range of 300 to 800 μm and
 a $d90_{,3}$-value in a range of 700 to 1500 μm,
 wherein the $d10_{,3}$-value is lower than the $d50_{,3}$-value and the $d50_{,3}$-value is lower than the $d90_{,3}$-value.

2. The crystal composition (CC) of claim 1, wherein the crystal composition (CC) comprises at least 95% by weight of the crystals (C), based on a total weight of the crystal composition (CC).

3. The crystal composition (CC) of claim 1, wherein the crystal composition (CC) has a bulk density in a range of 600 to 950 kg/m$^3$.

4. The crystal composition (CC) of claim 1, wherein an average aspect ratio of the crystals (C) is in a range of 0.2 to 1.

5. The crystal composition (CC) of claim 1, wherein an average sphericity of the crystals (C) is in a range of 0.75 to 0.85.

6. The crystal composition (CC) of claim 1, wherein a Hausner ratio is in a range of 1.05 to 1.27.

7. The crystal composition (CC) of claim 1, wherein a unit cell of the crystals (C) is monoclinic, space group C 2/m, cell lengths a=16.05 Å±0.05 Å, b=9.82 Å±0.05 Å, c=7.21 Å±0.05 Å, cell angles alpha 90°±0.1°, beta 95.7°±0.1°, gamma 90°±0.1°, and a cell volume 1131.5 Å$^3$±1 Å$^3$.

8. A crystal (C) consisting of
 (a) at least 95% by weight 4,4'-dichlorodiphenylsulfoxide,
 (b) 0 to 2% by weight of impurities, and
 (c) 0 to 3% by weight of an organic solvent (os),
 based in each case on a total weight of the crystal (C),
 wherein an outer surface of the crystal (C) comprises
 i) a six-sided base surface (bsu),
 ii) a six-sided top surface (tsu), and
 iii) six side surfaces (ssu1 to ssu6), joining the corresponding sides of the six-sided base surface (bsu) and the six-sided top surface (tsu).

9. The crystal (C) of claim 8, wherein the six-sided base surface (bsu), the six-sided top surface (tsu) and the six side surfaces (ssu1 to ssu6) account for at least 90% of the outer surface of the crystal (C).

10. The crystal (C) of claim 8, wherein a diameter (db) of the six-sided base surface (bsu) and a diameter (dt) of the six-sided top surface (tsu) are each independently in a range of 50 to 1500 μm.

11. The crystal (C) of claim 8, wherein a length (l1) of the first side surface (ssu1), a length (l2) of the second side surface (ssu2), a length (l3) of the third side surface (ssu3), a length (l4) of the fourth side surface (ssu4), a length (l5) of the fifth side surface (ssu5) and a length (l6) of the sixth side surface (ssu6) are each independently in a range of 100 to 3000 μm.

12. The crystal (C) of claim 8, wherein a ratio of an average of a diameter (db) of the six-sided base surface (bsu) and a diameter (dt) of the six-sided top surface (tsu) to an average of a length (l1) of the first side surface (ssu1), a length (l2) of the second side surface (ssu2), a length (l3) of the third side surface (ssu3), a length (l4) of the fourth side surface (ssu4), a length (l5) of the fifth side surface (ssu5) and a length (l6) of the sixth side surface (ssu6) is in a range of 0.2 to 1.

13. The crystal (C) of claim 8, wherein the impurities (b) comprise at least 90% by weight of one or more compounds selected from the group consisting of 2,4'-dichlorodiphenylsulfoxide, 3,4'-dichlorodiphenylsulfoxide, 2,2'-dichlorodiphenylsulfoxide, 4,4'-dichlorodiphenylsulfide, and one or more aluminum compounds based on a total weight of the impurities (b) comprised in the crystal (C).

14. The crystal composition (CC) of claim 1, obtained by a process comprising:
 I) cooling a first liquid mixture comprising 4,4'-dichlorodiphenylsulfoxide dissolved in an organic solvent (os) to obtain a suspension comprising crystallized 4,4'-dichlorodiphenylsulfoxide and the organic solvent (os),
 II) filtering the suspension obtained in I) to obtain a filtrate comprising 4,4'-dichlorodiphenylsulfoxide dissolved in the organic solvent (os), wherein the filtrate has a lower concentration of 4,4'-dichlorodiphenylsulfoxide compared to the first liquid mixture, and a filter residue comprising the crystallized 4,4'-dichlorodiphenylsulfoxide,
 III) concentrating the filtrate obtained in II) to obtain a second liquid mixture, wherein the second liquid mixture has a higher concentration of 4,4'-dichlorodiphenylsulfoxide compared to the filtrate,
 IV) recycling at least a part of the second liquid mixture obtained in III) into I), and
 V) drying the filter residue obtained in II) to obtain the crystal composition (CC).

15. The crystal (C) of claim 8, obtained by a process comprising:
 I) cooling a liquid mixture comprising 4,4'-dichlorodiphenylsulfoxide dissolved in an organic solvent (os) to obtain a suspension comprising crystallized 4,4'-dichlorodiphenylsulfoxide and the organic solvent (os),
 II) filtering the suspension obtained in I) to obtain a filtrate comprising 4,4'-dichlorodiphenylsulfoxide dissolved in the organic solvent (os), wherein the filtrate has a lower concentration of 4,4'-dichlorodiphenylsulfoxide compared to the liquid mixture, and a filter residue comprising the crystallized 4,4'-dichlorodiphenylsulfoxide,
 V) drying the filter residue obtained in II) to obtain a crystal composition (CC), and VI) separating a crystal (C) from the crystal composition (CC) obtained in V).

16. A method of producing a monomer, polymer, or pharmaceutical, the method comprising reacting a crystal composition (CC) as an intermediate,
- wherein the crystal composition (CC) comprises crystals (C), wherein the crystals (C) consist of
- (a) at least 95% by weight of 4,4'-dichlorodiphenylsulfoxide,
- (b) 0 to 2% by weight of impurities, and
- (c) 0 to 3% by weight of an organic solvent (os),
- based on a total weight of the crystals (C) comprised in the crystal composition (CC), wherein the crystal composition (CC) has
- a $d10_{,3}$-value in a range of 100 to 400 μm,
- a $d50_{,3}$-value in a range of 300 to 800 μm and
- a $d90_{,3}$-value in a range of 700 to 1500 μm,
- wherein the $d10_{,3}$-value is lower than the $d50_{,3}$-value and the $d50_{,3}$-value is lower than the $d90_{,3}$-value.

* * * * *

UNITED STATES PATENT AND TRADEMARK OFFICE
CERTIFICATE OF CORRECTION

PATENT NO. : 10,975,024 B2
APPLICATION NO. : 16/784287
DATED : April 13, 2021
INVENTOR(S) : Thiel et al.

Page 1 of 1

It is certified that error appears in the above-identified patent and that said Letters Patent is hereby corrected as shown below:

On the Title Page

Item (54) and in the Specification, Column 1, Line 3-4, "4,4#-dichlorodiphenylsulfoxide" should read -- 4,4'-dichlorodiphenylsulfoxide --.

In the Specification

Column 3, Line 51, "(1.01325" should read -- (1,01325 --.

Column 4, Line 4, "tappered" should read -- tapered --;

Column 4, Line 8, "tappered" should read -- tapered --;

Column 4, Line 13, "tappered" should read -- tapered --.

Column 6, Line 56, "A means Angstrom" should read -- Å means Ångström --.

Column 10, Line 46, "Monchlorobenzene" should read -- Monochlorobenzene --.

Column 13, Line 56, "diethyl ether" should read -- diethylether --.

Signed and Sealed this
First Day of March, 2022

Drew Hirshfeld
*Performing the Functions and Duties of the
Under Secretary of Commerce for Intellectual Property and
Director of the United States Patent and Trademark Office*